US011511407B2

(12) United States Patent
Nino (10) Patent No.: US 11,511,407 B2
(45) Date of Patent: Nov. 29, 2022

(54) SINGLE USE INTEGRATED SPEED REDUCTION AND GEARLESS DEVICE

(71) Applicant: ECA MEDICAL INSTRUMENTS, Thousand Oaks, CA (US)

(72) Inventor: John Nino, Newbury Park, CA (US)

(73) Assignee: ECA Medical Instruments, Inc., Thousand Oaks, CA (US)

( * ) Notice: Subject to any disclaimer, the term of this patent is extended or adjusted under 35 U.S.C. 154(b) by 270 days.

(21) Appl. No.: 16/761,494

(22) PCT Filed: Nov. 2, 2018

(86) PCT No.: PCT/US2018/059067
§ 371 (c)(1),
(2) Date: May 4, 2020

(87) PCT Pub. No.: WO2019/090155
PCT Pub. Date: May 9, 2019

(65) Prior Publication Data
US 2021/0172499 A1 Jun. 10, 2021

Related U.S. Application Data

(60) Provisional application No. 62/580,786, filed on Nov. 2, 2017.

(51) Int. Cl.
*B25F 5/00* (2006.01)
*A61B 90/00* (2016.01)
(Continued)

(52) U.S. Cl.
CPC .......... *B25F 5/001* (2013.01); *A61B 17/1624* (2013.01); *B23B 45/008* (2013.01);
(Continued)

(58) Field of Classification Search
CPC . F16H 1/28; F16H 55/06; F16H 57/08; F16H 57/082; A61B 17/1624; B23B 45/008
See application file for complete search history.

(56) References Cited

U.S. PATENT DOCUMENTS 5,207,697 A * 5/1993 Carusillo ........... A61B 17/1628
408/124
5,553,675 A * 9/1996 Pitzen .................... H02K 7/116
173/217

(Continued)

OTHER PUBLICATIONS

Search Report and Written Opinion of International Patent Application No. PCT/US2018/059067; dated Feb. 7, 2019.
(Continued)

*Primary Examiner* — Tinh Dang
(74) *Attorney, Agent, or Firm* — Ferguson Case Orr Paterson (57) ABSTRACT

A single use integrated disposable rotational speed reduction assembly having a shaft assembly, a housing, an output assembly, and a plurality of planetary gears each having a plurality of gear teeth. The shaft assembly is configured to cause rotation of the planetary gears with a sun gear. The rotation of the planetary gears is configured to cause rotation of an output shaft, with a reduction of rotational speed relative to the rotation of the shaft assembly. One or more gear components or spacers can be configured to fail after a predetermined number of use cycles.

15 Claims, 9 Drawing Sheets

(51) Int. Cl.
  *A62B 17/00* (2006.01)
  *A61B 17/16* (2006.01)
  *B23B 45/00* (2006.01)
  A61B 17/00 (2006.01)
  B25B 23/14 (2006.01)

(52) U.S. Cl.
  CPC .............. *A61B 2017/00367* (2013.01); *A61B 2017/00831* (2013.01); *A61B 2560/0285* (2013.01); *B23B 2260/07* (2013.01); *B23B 2260/11* (2013.01); *B25B 23/14* (2013.01)

(56) References Cited

U.S. PATENT DOCUMENTS

| | | | | |
|---|---|---|---|---|
| 5,993,454 A * | 11/1999 | Longo | ................... | B23Q 5/048 606/85 |
| 6,415,735 B1 | 7/2002 | Rogers | | |
| 7,850,620 B2 * | 12/2010 | Miller | ................... | A61B 50/33 600/568 |
| 9,295,815 B2 * | 3/2016 | Stevens | ........... | A61M 25/09041 |
| 10,085,757 B2 * | 10/2018 | Detry | ................ | A61B 17/1624 |
| 2008/0287247 A1 * | 11/2008 | Pusateri | ................. | B25B 21/00 81/436 |
| 2011/0196375 A1 | 8/2011 | Li et al. | | |
| 2013/0123921 A1 * | 5/2013 | Jones | ................... | A61F 2/4601 623/16.11 |
| 2013/0226192 A1 | 8/2013 | Nino | | |
| 2013/0276598 A1 | 10/2013 | Ivinson | | |
| 2013/0303330 A1 * | 11/2013 | Stevens | .............. | A61M 25/0113 475/349 |
| 2015/0148176 A1 * | 5/2015 | Schroeder | .......... | A61B 17/1624 464/33 |

OTHER PUBLICATIONS

EPO Communication pursuant to Rules 70(2) and 70a(2) EPC of Application No. 18872657.4 dated Nov. 30, 2021.
Extended European Search Report of Application No. 18872657.4 dated Nov. 12, 2021.

\* cited by examiner

SECTION D-D

SINGLE USE INTEGRATED SPEED REDUCTION AND GEARLESS DEVICE

CROSS-REFERENCE TO RELATED APPLICATIONS

This application is a national phase application of International Application No. PCT/US2018/059067, filed on Nov. 2, 2018, which claims the benefit of U.S. Provisional Application No. 62/580,786 filed Nov. 2, 2017. Each application referenced in this paragraph is incorporated by reference in its entirety as if fully set forth herein.

TECHNICAL FIELD

This disclosure relates generally to single use rotational speed reduction devices and methods.

BACKGROUND

Tools used in different industries operate at many different speeds, and controlling the speed of operation is sometimes necessary. The need for carefully controlled speed of resecting tools often used in surgery is well known. Tools used during medical procedures must meet a predetermined level of sterilization. The financial and societal costs of infections caused by improperly sterilized items used during surgery are significant. Maintaining and sterilizing speed reduced powered tools used during medical procedures adds to the cost of health care.

DISCLOSURE

Many rotational tools (e.g. drills) operate at very high velocities, and it is sometimes necessary to reduce or limit how fast such tools spin. In the medical field, torque limiting devices in the operational theater are useful to reduce variables associated with resection and fastening medical devices. However, unrestricted high-speed device operation may add unnecessary risk variables to a procedure.

According to aspects of some exemplary implementations of the disclosure, the disclosure provides integrated rotational speed reduction assemblies having a shaft assembly, a housing, an output assembly, and a plurality of planetary gears each having a plurality of gear teeth. In some implementations of the integrated rotational speed reduction assemblies, the shaft assemblies can have a sun gear with a plurality of gear teeth, the shaft assembly can provide for the mating between the housing and the output assembly via one or more retaining features provided on the shaft assembly. In some implementations, the output assembly can have a plurality of pin guides, with each pin guide mating with one of the plurality of planetary gears to prevent relative axial movement between each mated pin guide and planetary gear but allowing for relative axial rotation between each mated pin guide and planetary gear, the housing can have a gear ring of a plurality of gear teeth disposed on an interior surface of the housing, with the gear ring configured to engage with the gear teeth of the planetary gears, and at least a portion of the output assembly can be configured to rotate in response to rotation of the shaft assembly, via engagement between the sun gear and the planetary gears, engagement between the planetary gears and the gear ring.

According to aspects of some exemplary implementations of the disclosure, methods of reducing rotational velocity of a tool include a step of engaging a tool with an integrated rotational speed reduction assembly as it is described in any of the exemplary implementations throughout this application. In some implementations, the methods can include a step of operating the tool once it is engaged with the integrated rotational speed reduction assembly.

DRAWINGS

The summary, as well as the following detailed description, is further understood when read in conjunction with the appended drawings. For the purpose of illustrating the disclosure, there are shown in the drawings exemplary implementations of the disclosure; however, the disclosure is not limited to the specific methods, compositions, and devices disclosed. In addition, the drawings are not necessarily drawn to scale.

All reference numerals, designators, and call-outs in the figures are hereby incorporated by this reference as fully set forth herein. The failure to number an element in a figure is not intended to waive any rights, and unnumbered references may also be identified by alpha characters in the figures.

FURTHER DISCLOSURE

Some aspects of the disclosure will now be described in further detail with reference to the drawings, wherein like reference numbers refer to like elements throughout, unless specified otherwise. Certain terminology is used in the following description for convenience only and is not limiting.

For the purpose of illustrating the subject matter, there are shown in the drawings exemplary implementations of the subject matter; however, the presently disclosed subject matter is not limited to the specific methods, devices, and systems disclosed. In addition, the drawings are not necessarily drawn to scale.

The present disclosure may be understood more readily by reference to the following description taken in connection with the accompanying Figures and Examples, all of which form a part of this disclosure. It is to be understood that this invention is not limited to the specific products, methods, conditions or parameters described or shown herein, and that the terminology used herein is for the purpose of describing particular exemplary implementations by way of example only and is not intended to be limiting of any claimed invention. Similarly, unless specifically otherwise stated, any description as to a possible mechanism or mode of action or reason for improvement is meant to be illustrative only, and the invention herein is not to be constrained by the correctness or incorrectness of any such suggested mechanism or mode of action or reason for improvement. Throughout this text, it is recognized that the descriptions refer to apparatuses and methods of using said apparatuses. That is, where the disclosure describes or claims a feature or embodiment associated with an apparatus or a method of using an apparatus, it is appreciated that such a description or claim is intended to extend these features or embodiment to exemplary implementations in each of these contexts (i.e., apparatuses, methods of making, and methods of using).

In the present disclosure, the singular forms "a, "an, and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about, it will be understood that the particular value forms another exemplary implementation. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include every value within that range.

It is to be appreciated that certain features of the disclosure which are, for clarity, described herein in the context of separate exemplary implementations, may also be provided in combination in a single implementation. That is, unless obviously incompatible or specifically excluded, each individual exemplar is deemed to be combinable with any other exemplar(s) and such a combination is considered to be another exemplar. Conversely, various features of the disclosure that are, for brevity, described in the context of a single exemplar, may also be provided separately or in any sub-combination. Finally, while an exemplar may be described as part of a series of steps or part of a more general structure, each said step may also be considered an independent exemplar in itself, combinable with others.

The transitional terms "comprising," "consisting essentially of," and "consisting" are intended to connote their generally accepted meanings in the patent vernacular; that is, (i) "comprising," which is synonymous with "including," "containing," or "characterized by," is inclusive or open-ended and does not exclude additional, un-recited elements or method steps; (ii) "consisting of" excludes any element, step, or ingredient not specified in the claim; and (iii) "consisting essentially of" limits the scope of a claim to the specified materials or steps "and those that do not materially affect the basic and novel characteristic(s)." Exemplars described in terms of the phrase "comprising" (or its equivalents), also provide, as exemplars, those which are independently described in terms of "consisting of" and "consisting essentially" of.

When a list is presented, unless stated otherwise, it is to be understood that each individual element of that list, and every combination of that list, is a separate exemplar. For example, a list of exemplars presented as "A, B, or C" is to be interpreted as including the exemplars. "A," "B," "C," "A or B," "A or C," "B or C," or "A. B, or C."

Throughout this specification, words are to be afforded their normal meaning, as would be understood by those skilled in the relevant art. However, so as to avoid misunderstanding, the meanings of certain terms will be specifically defined or clarified.

Figure 1:
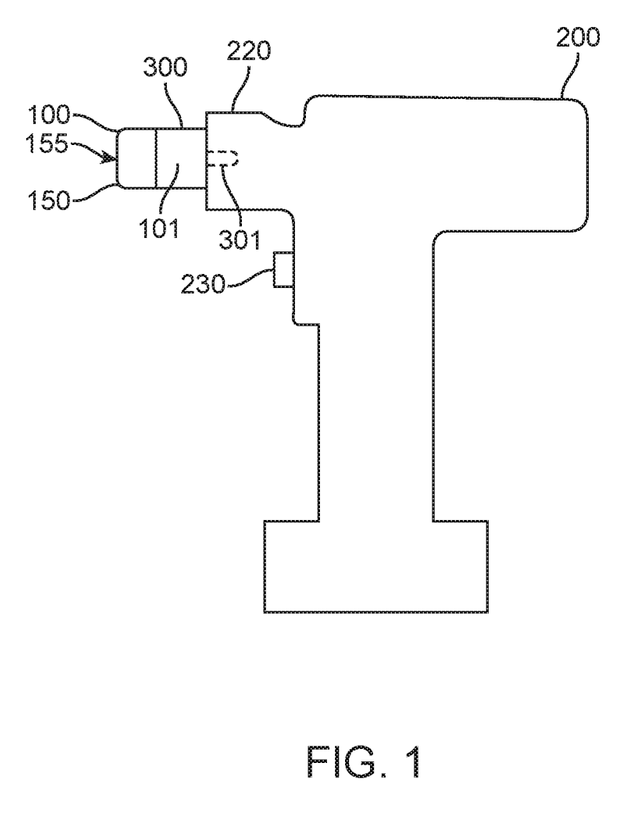
FIG. 1 is a schematic illustration of a side view of an exemplary implementation of a rotational speed reduction device.
Figure 2:
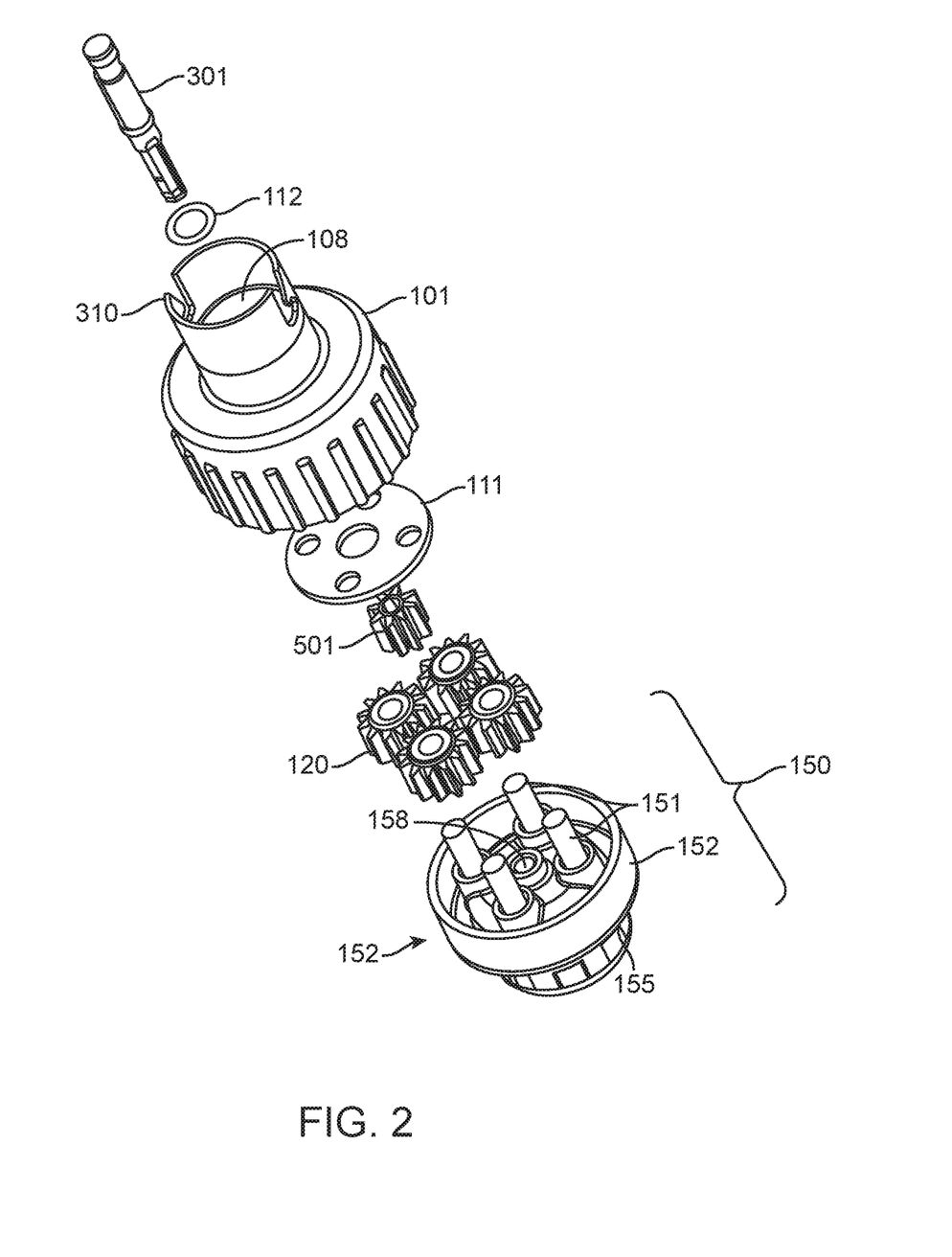
FIG. 2 is an exploded view of an exemplary implementation of an integrated rotational speed reduction assembly.
Figure 3:
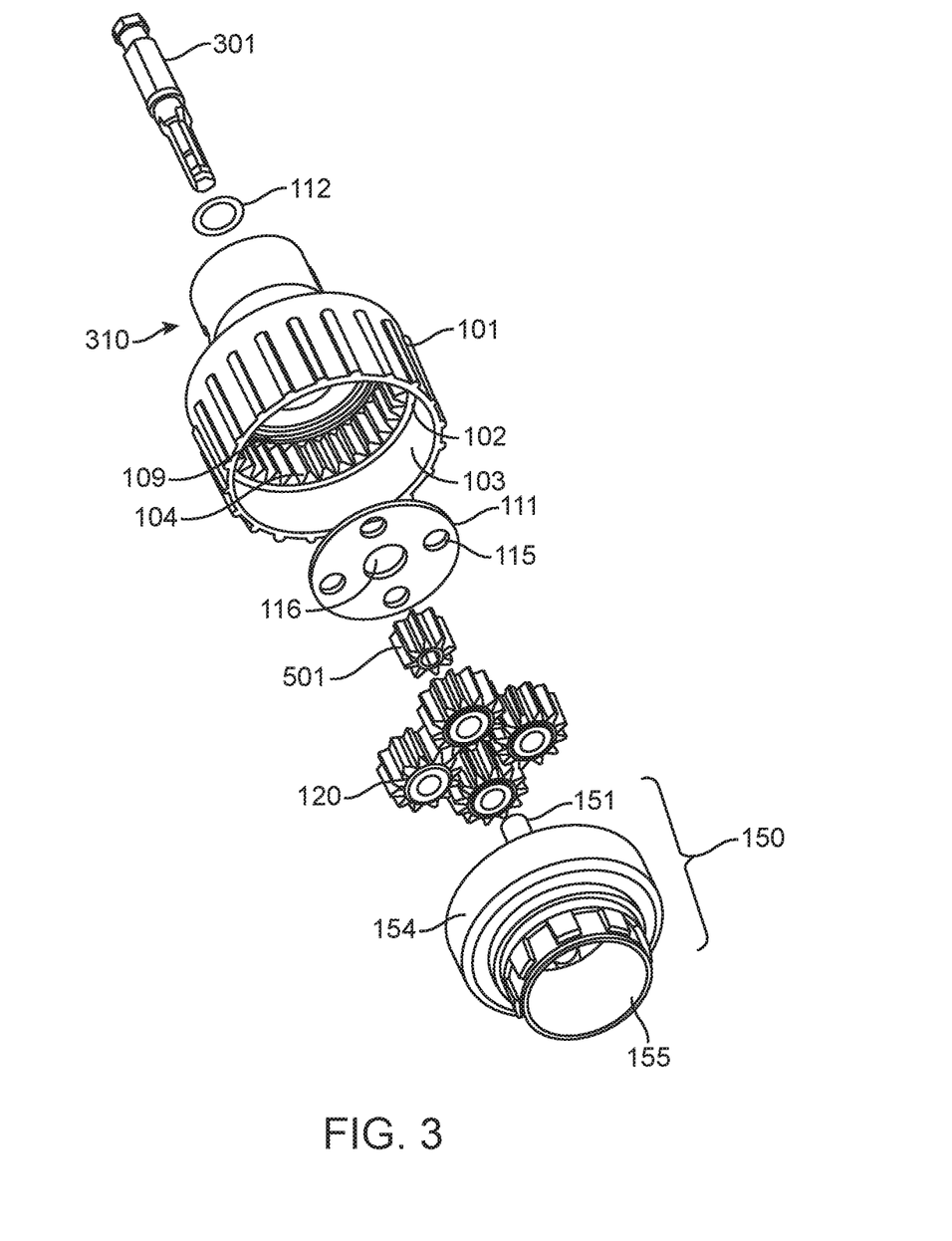
FIG. 3 is an exploded view from a different angle of the integrated rotational speed reduction assembly shown in FIG. 2.
Figure 4:
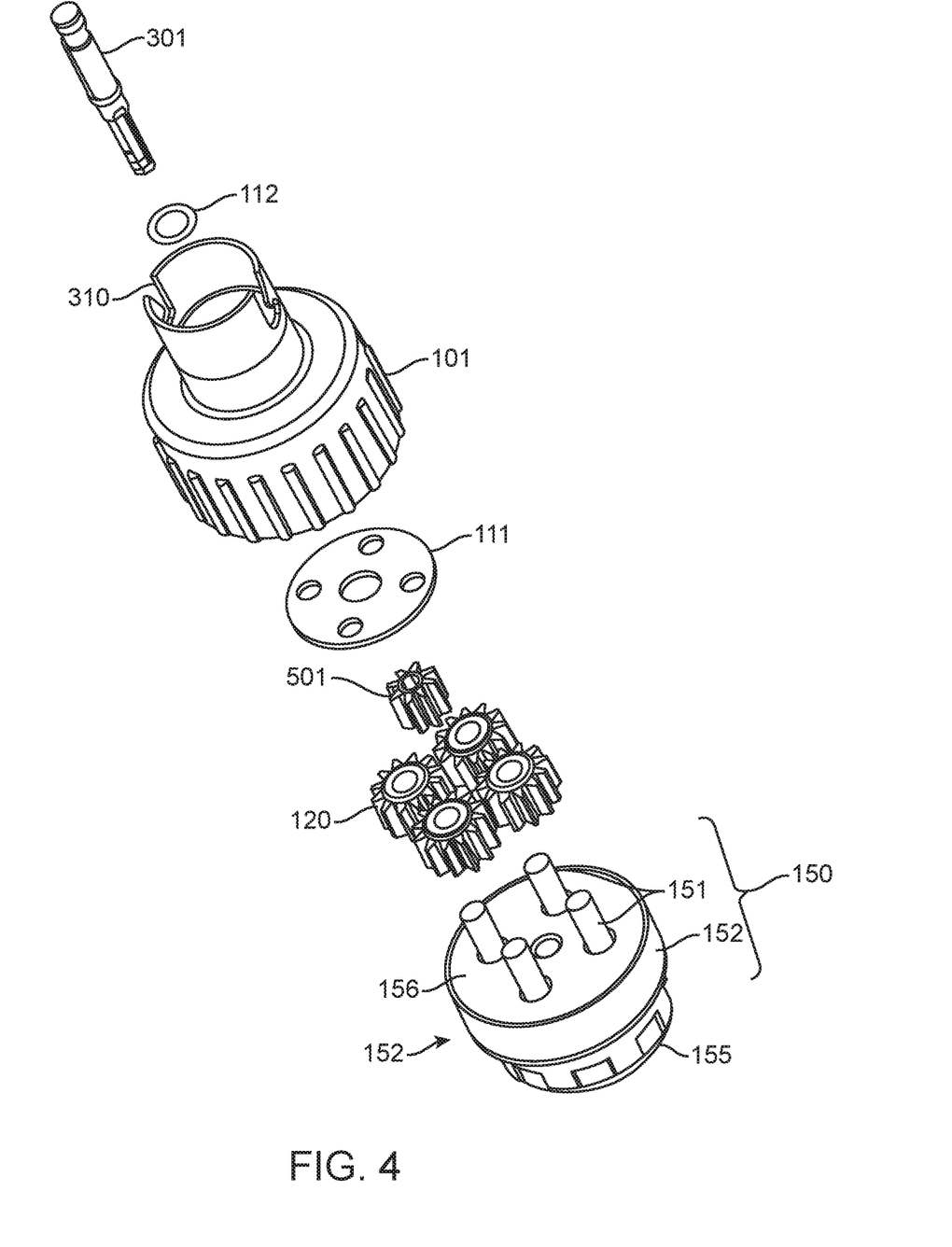
FIG. 4 is an exploded view of an exemplary implementation of an integrated rotational speed reduction assembly.
Figure 5:
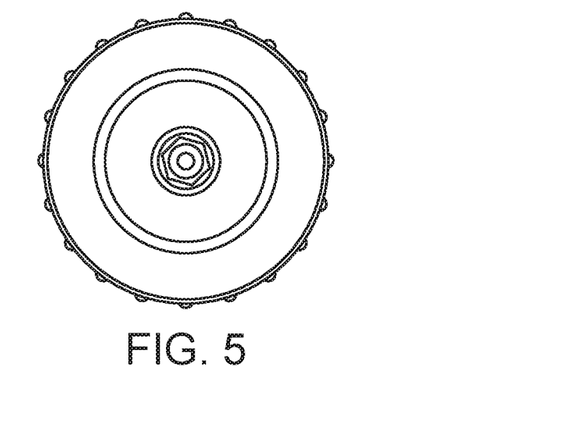
FIG. 5 is a top view of an exemplary implementation of an integrated rotational speed reduction assembly.
Figure 6:
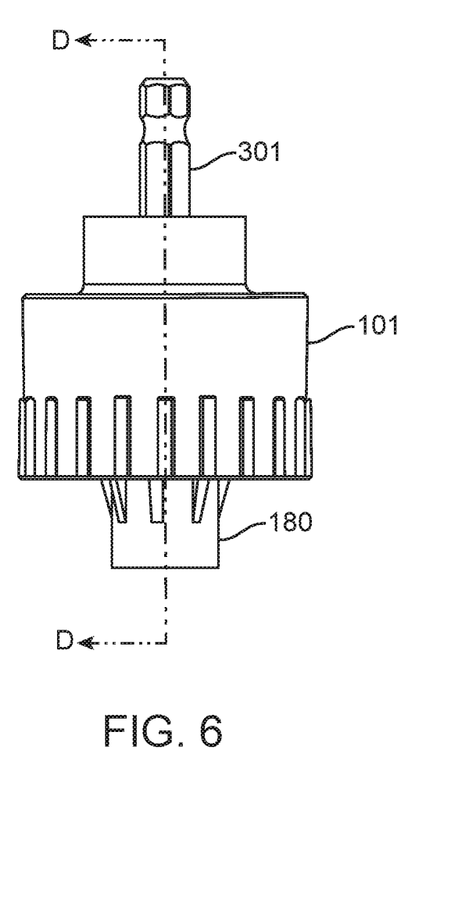
FIG. 6 is a side view of the integrated rotational speed reduction assembly shown in FIG. 5.
Figure 7:
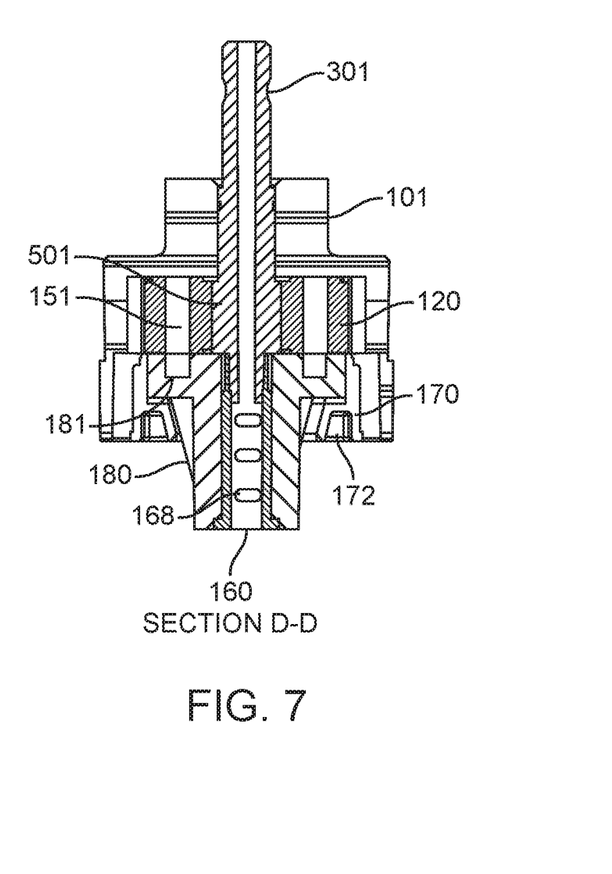
FIG. 7 is a cross-sectional view of the integrated rotational speed reduction assembly shown in FIGS. 5 and 6.
Figure 8:
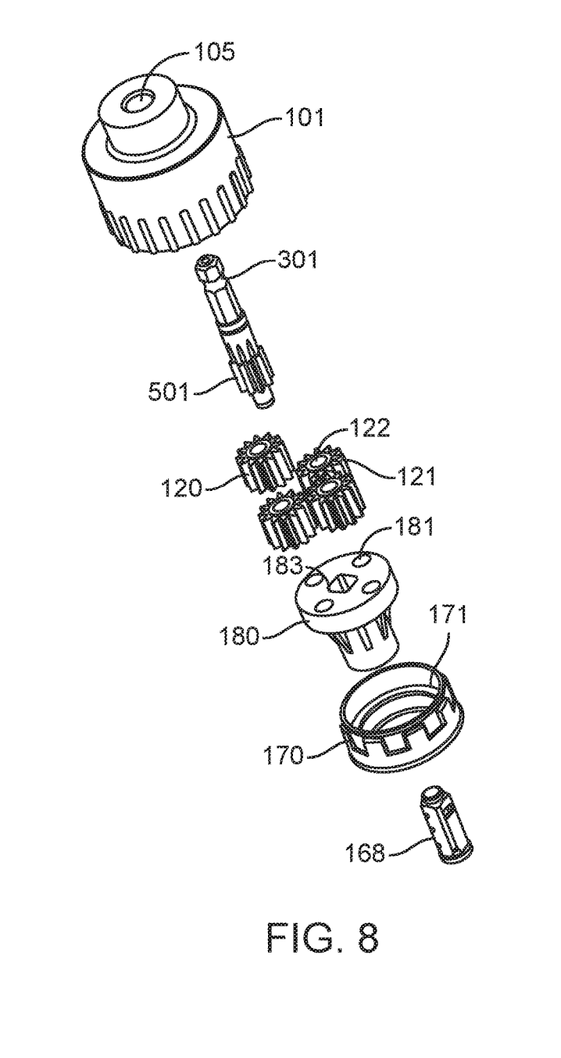
FIG. 8 is an exploded view of the integrated rotational speed reduction assembly shown in FIGS. 5-7.
Figure 9:
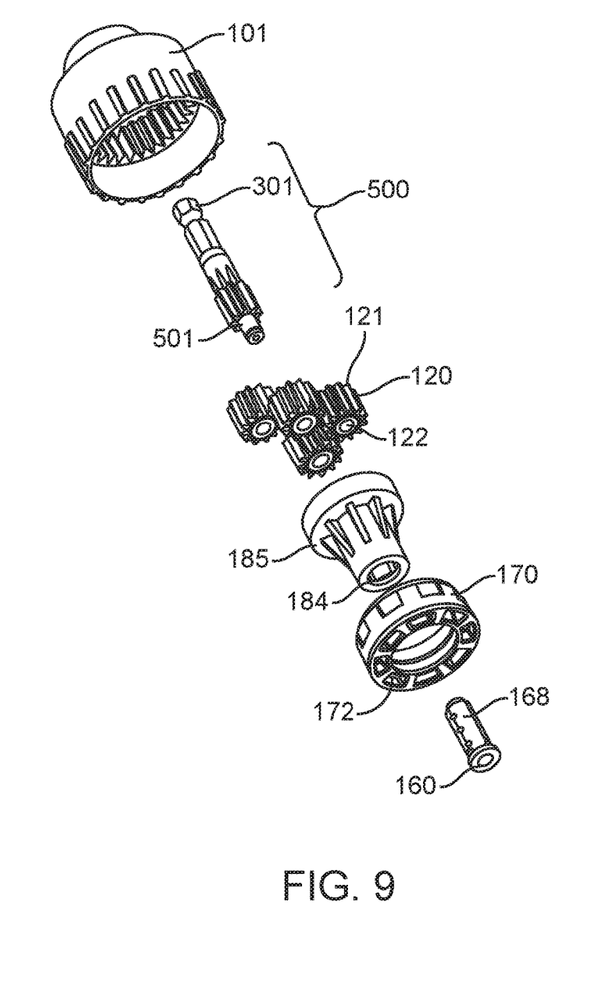
FIG. 9 is an exploded view from a different angle of the integrated rotational speed reduction assembly shown in FIGS. 5-8.

FIG. 1 depicts aspects of an implementation of a medical power tool system incorporating implementations of an integrated rotational speed reduction assembly 100. A medical power tool 200 with one or more actuation buttons 230 and an output mechanism 220 can be used. Output mechanism 220 can include a recessed opening that contains the output connection. Many standard types of output connections are known to those of skill in the art, including AO small, AO large, Trinkle, Hudson, Harris, and Zimmer. Integrated rotational speed reduction assembly 100 has a housing 101 with an interface system 300, which can be connected to output mechanism 220 and affixed in place such that the output connection is connected to a drill connection shaft 301 that is part of a shaft assembly 500 within the integrated rotational speed reduction assembly 100. Housing 101 can be provided with an interface system 300 having a retaining feature 310 that is used to lock the housing 101 in place relative to the output mechanism 220, such that the housing 101 does not rotate, but drill connection shaft 301 may rotate as it is driven by the medical power tool 200. A quick-turn retaining feature 310 is depicted in FIGS. 2-4, but alternative retaining features such as helical threading or fasteners could also be used. Retaining features of interface system 300 have been omitted from FIGS. 5-9 and 12-13 for illustrative purposes, but any suitable retaining feature described herein could be provided on housing 101. Drill connection shaft 301, also referred to herein as a drive shaft, can be configured with a variety of end profiles and connection types in order to interface with the output mechanism utilized in the particular power tool 200 being used in the system. Actuation button 230 can be utilized by a user to activate an internal motor of the power tool 200 (not shown) that transmits rotational force to output mechanism 220 and causes the mechanism to rotate.

Housing 101 is configured to interface with an output assembly 150 to enclose internal planetary gear components and form an integrated rotational speed reduction assembly 100. Housing 101 is mated to the output assembly 150. The housing 101 and output assembly 150 can be mated with a snap-fit connection, welded, or connected with another suitable manner, provided that at least any planet carrier portion of the output assembly 150 can rotate relative to the housing 101, as described more fully elsewhere herein. In some exemplary implementations, the housing 101 and output assembly 150 are held together by the drill connection shaft 301, which has retaining features 505/506 which interface with portions of the housing 101 and the output assembly 150 to hold them in close proximity, as described more fully elsewhere herein. At a distal end 155 of the output assembly 150, a workpiece interface is included to provide for transfer of rotational torque to a workpiece (not shown). In FIGS. 2-4, 12 and 13 the workpiece interface is illustrated conceptually as a stepped profile around the outer surface of the distal end 155, but in other implementations the workpiece interface can be a tip connection 160 disposed within a central portion of the distal end 155 or any other element that is rigidly fixed to rotate with the planet carrier portion of the output assembly 150. The tip connection 160 can be configured to interface with a workpiece or another workpiece-engaging component (not shown or further described herein). Tip connection 160 can be implemented as one of many connection types, including a female AO type connection, AO small, AO large, Trinkle, Hudson, Harris, Zimmer, ⅝-inch square, socket wrenches, or other profiles. In some implementations, tip connection 160 can be configured with a workpiece-engaging profile for direct use on a workpiece or fastener. Some suitable configurations for tip connection 160 and workpiece engaging tips are disclosed in U.S. Patent Publication No. US2013/0226192 A1 which is incorporated by reference herein in its entirety. In some implementations tip connection 160 can also be configured to accept a keyed or keyless drill chuck with jaws that can clamp a variety of tools including drills and drivers.

Figure 10:
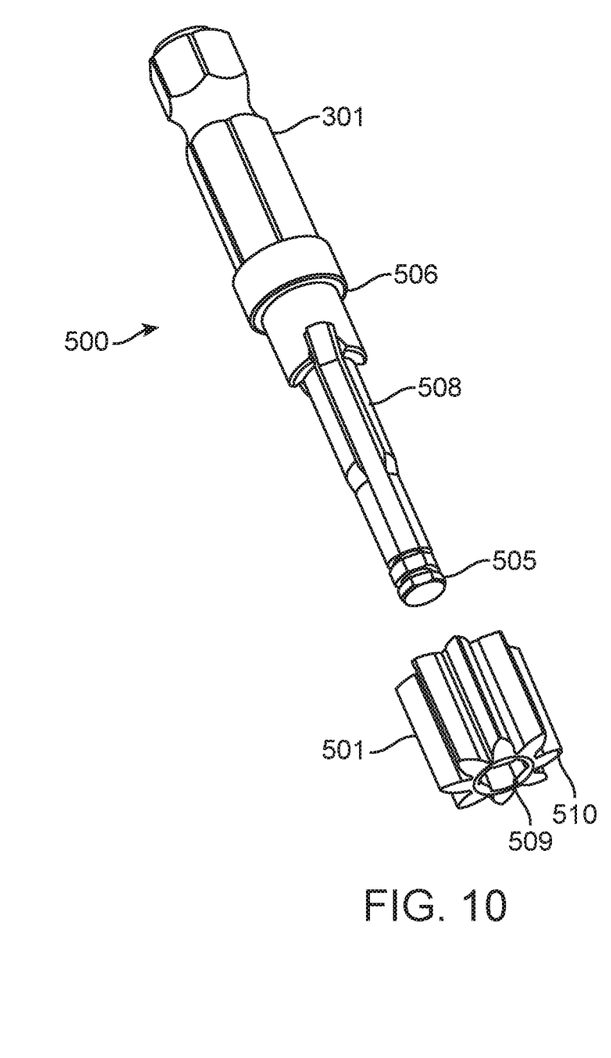
FIG. 10 is an exploded view of aspects of an exemplary implementation of an integrated rotational speed reduction assembly.
Figure 11:
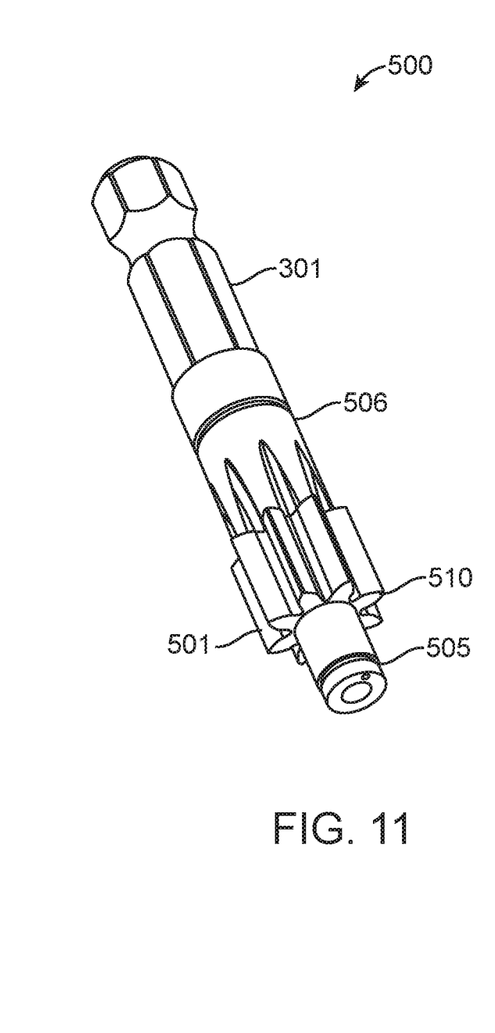
FIG. 11 is a perspective view of aspects of an exemplary implementation of an integrated rotational speed reduction assembly.
Figure 12:
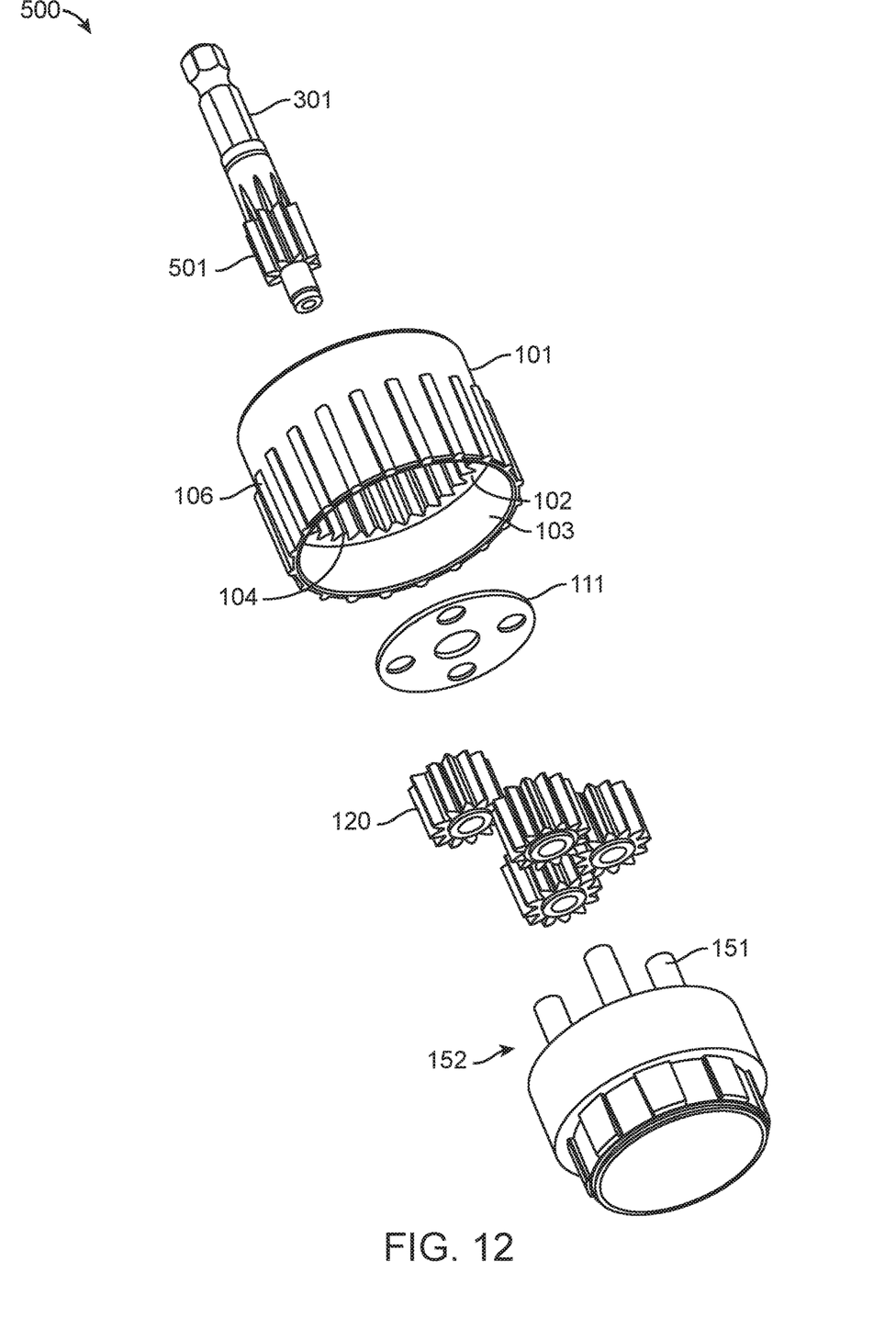
FIG. 12 is an exploded view of an exemplary implementation of an integrated rotational speed reduction assembly.
Figure 13:
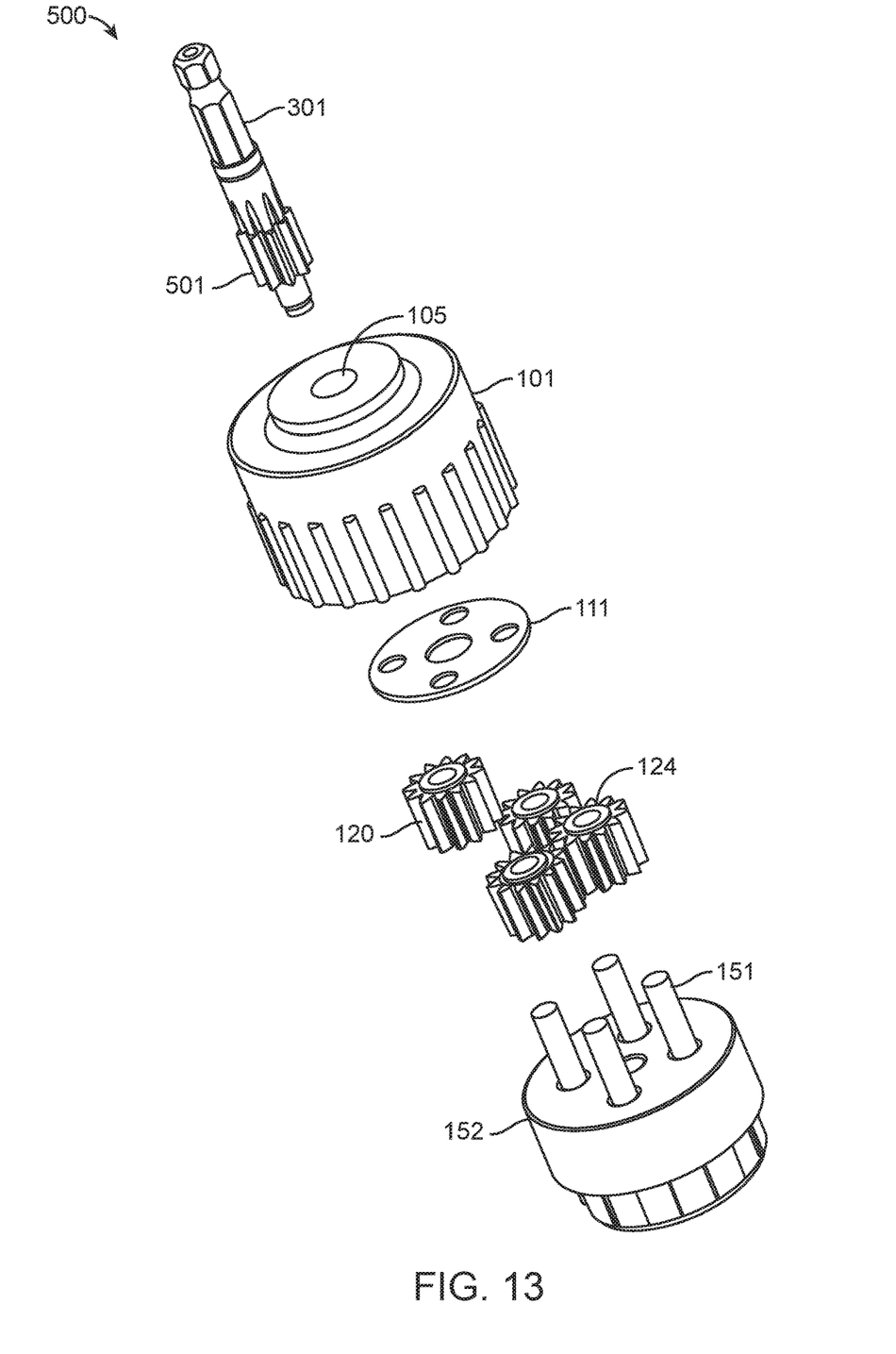
FIG. 13 is an exploded view from a different angle of the integrated rotational speed reduction assembly shown in FIG. 12

In some implementations a shaft assembly 500 is configured to receive torque input to the integrated rotational speed reduction assembly 100 via the drill connection shaft 301. Some implementations of shaft assembly 500 are shown in FIGS. 10 and 11. The shaft assembly 500 can be formed as a singular piece, or in the alternative, it may be an assembly of multiple pieces. The shaft assembly 500 may be solid or hollow. The shaft assembly 500 may be solid throughout, hollow throughout, or solid in one or more locations and hollow in one or more locations. The shaft assembly 500, sun gear and/or planetary gears may include various materials, such as, but not limited to, metals, plastics, or a combination of metals and plastics. It may be made of metals, such as, but not limited to stainless steel, aluminum, or other metal alloys. In a non-limiting exemplary implementation, the shaft may be made of SAE 316 grade stainless steel. The shaft assembly 500, sun gear and/or planetary gears may include various materials, such as, but not limited to, metals, plastics, or a combination of metals and plastics. It may be made of metals, such as, but not limited to stainless steel, aluminum, or other metal alloys. In a non-limiting exemplary implementation, the shaft may be made of SAE 316 grade stainless steel. The shaft assembly 500, sun gear and/or planet gears may also be made of plastics, such as, but not limited to high-density polyethylene, low-density polyethylene, polyvinyl chloride, polypropylene, acrylonitrile butadiene styrene, polycarbonate, polyurethane, malcimide, bismaleimide, melamine formaldehyde, polyetheretherketone, polymethyl methacrylate, polytetrafluoroethylene (PTFE), fluorinated ethylene propylene (FEP), polyacetals (Delrin, Celcon), aliphatic and amorphous grades of nylon polyamides, polymethylpentene, polypropylenes, or a combination of one or more of plastics in this list. The selection of materials, may in part, be associated with the single use cycle requirements of a device.

The shaft assembly 500 can provide for the mating between housing 101 and output assembly 150 through the incorporation of retaining features 505/506. Retaining features 505/506 may be raised edges, slits that snap-fit with raised features on the housing 101 or the output assembly 150, slits or holes that are configured to hold retaining rings or cotter pins, or other systems known in the art that can serve to prevent relative axial movement between the retaining features 505/506 and the corresponding component. In some exemplary implementations a low friction spacer 112 is disposed between a raised lip retaining feature 506 and a surface 108 of the housing 101. The retaining features serve to provide retention of the housing 101 and the output assembly 150 within close proximity of each other, retaining the housing 101 and the output assembly 150 between the two retaining features 505/506, as shown in the Figures. Shaft assembly 500 includes a sun gear 501 with a plurality of gear teeth 510.

In some instances one or more of the drive shaft 301, the sun gear 501 and at least one planet gear 120 are constructed of a material which is frangible or will otherwise fail after a predetermined number of cycles. A cycle for purposes of understanding the exemplar is the distance to complete one rotation of one of the drive shaft and output assembly 150. In some preferred implementations, any fragments of the one or more of the drive shaft 301, the sun gear 501, and at least one planet gear 120 that result from frangibility or other failure will be retained within the internal cavity of the housing 101.

Preordained failure is used as an aspect of systems and methods disclosed herein to render the disposable device inoperable (within its use parameters) after a predetermined number of use cycles. In the medical arena, single use tools benefit from lower cost materials which are suitable for limited use cycles. Tool construction for a single use device also allows for designs which may have cavities and portions not amenable to subsequent re-sterilization, thus further providing opportunity for a reduction in health care costs. Risks associated with the improper reuse of single use or disposable tools include but are not limited to contamination, infection, failure during reuse, out of specification performance, damage to the mechanism during attempted re-sterilization. In some instances, about 500 cycles at a predetermined force of Newton-meters is the preordained failure. In some instances, between about 400 and about 600 cycles at a predetermined force of Newton-meters is the preordained failure. In some instances, between about 200 and about 400 cycles at a predetermined force of Newton-meters is the preordained failure. In some instances, between about 500 and about 1000 cycles at a predetermined force of Newton-meters is the preordained failure.

In certain implementations, preordained failure can be determined by the construction of one or more of the drive shaft 301, the sun gear 501 and at least one planet gear 120 of a material which is frangible or will otherwise fail after a predetermined number of cycles. The one or more of the drive shaft 301, the sun gear 501, and at least one planet gear 120 can be constructed as a component designed for embrittlement or weakening during a chosen sterilization process. In some implementations, the component can be embrittled or weakened via a gamma sterilization procedure that can be used to sterilize a fully assembled disposable tool or device prior to use. In certain implementations, the preordained failure can be determined by including a wt/wt % of one or more gamma-radiation-sensitive materials in the one or more components. Upon exposure to gamma radiation, gamma-radiation-sensitive materials undergo a reduction of one or more of tensile strength, impact resistance, hardness, compressive strength, tear strength, and flexural properties, such that the materials are embrittled due to the exposure. In some implementations, the one or more gamma-radiation-sensitive materials undergo embrittlement at an exposure less than about 200 kGy, 150 kGy, 100 kGy, 95 kGy, 90 kGy, 85 kGy, 80 kGy, 75 kGy, 70 kGy, 65 kGy, 60 kGy, 55 kGy, 50 kGy, 45 kGy, 40 kGy, 35 kGy, 30 kGy, 25 kGy, 20 kGy, 15 kGy, 10 kGy, or 5 kGy. In some implementations the one or more gamma-radiation-sensitive materials can be polytetrafluoroethylene (PTFE), fluorinated ethylene propylene (FEP), polyoxymethylene/polyacetals (Delrin, Celcon), aliphatic and amorphous grades of nylon polyamides, polymethylpentene, polypropylenes, or combinations thereof. In certain implementations, the one or more gamma-radiation-sensitive materials can be incorporated throughout one or more components as a wt/wt % of the gamma-radiation-sensitive material in all regions of the one or more components. In other implementations, the one or more gamma-radiation-sensitive materials can be incorporated in one or more components in a particular region of the one or more components, while the remaining regions of the one or more components are substantially free of any gamma-radiation-sensitive material, providing a desired wt/wt % for the one or more components when considered as a whole. In some implementations, the particular region of the one or more components having one or more gamma-radiation-sensitive materials can be one or more teeth of a gear. The wt/wt % of one or more gamma-radiation-sensitive materials in the one or more components can be about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

Some implementations of shaft assembly 500 are formed from a drill connection shaft 301 that mates with a separate component sun gear 501. In some implementations, the sun gear 501 includes an opening 509 through a central axis, and the opening 509 can have a geometric profile that is complementary with a shaped portion 508 of the drill connection shaft 301. The corresponding geometric profiles provide a rigid connection that allows for the transmission of torque.

In some implementations of the shaft assembly 500, the assembly is formed as one integral component that includes the sun gear 501 and the drive shaft 301. Shaft assembly 500 can be formed by machining or by molding.

In some implementations, the entire output assembly 150 rotates relative to the housing 101. As shown in FIGS. 2-4 and 12-13, output assembly 150 can comprise an output shaft 152 and a plurality of planet gear carrier pins 151. The planet gear carrier pins 151 can be formed integrally with output shaft 152 or can be press-fit or fastened to the output shaft 152, provided that the axes of the planet gear carrier pins 151 are aligned parallel to each other and extend perpendicularly from the proximal face 156 of the output shaft 152 from which they protrude. The proximal face 156 is disposed on the opposite end of the output assembly 150 from the distal end 155. The output shaft 152 and planet gear carrier pins 151 are rigidly connected such that any rotational torque forces placed on the planet gear carrier pins 151 are transferred to the output shaft 152. An outer surface 154 of the output assembly can rotate past an interior surface 103 within the housing. In some implementations, the proximal face 156 can be provided with voids, slots, or holes (not shown in the Figures) to act as catching volumes to retain at least a portion of any debris or degraded portions that may break off of internal components.

In some implementations, one or more portions of the output assembly 150 rotate relative to the housing 101. As shown in FIGS. 5-9, output assembly 150 can comprise a retainer 170 and a planet carrier 180. Planet carrier 180 is formed with an axial opening having a proximal end 183 and distal end 184. In some implementations, the planet carrier 180 can include a plurality of mounting holes 181 configured to mount planet gear carrier pins 151 (not depicted in exploded views in FIGS. 8 and 9). In some implementations, the planet carrier 180 includes integral planet gear carrier pins 151. The proximal end 183 of the axial opening is configured to receive and mate with retaining feature 505 on the distal end of the shaft assembly 500. In some exemplary implementations, a protrusion or ridge within the proximal end 183 can mate with retaining feature 505 in a snap-fit engagement. The distal end 184 of the axial opening can be configured to mate with a workpiece or another workpiece-engaging component (not depicted herein), with connection features the same as the tip connection 160 described above. In some implementations, the distal end 184 of the axial opening of planet carrier 180 is configured to receive and mate with an output shaft insert 168, which contains a tip connection 160. In some exemplary implementations, retaining feature 505 engages with a portion of the output shaft insert 168 to connect the two components along their central axis but allow for relative rotation therebetween. The retainer 170 can be provided with an inner surface 171 which abuts against a surface 185 of the planet carrier 180. In some implementations a washer can be provided in between the surfaces 171/185 to reduce friction. The retainer 170 is mated with the housing 101 and connected via snap-fit, welding, threaded connection, or other methods of connection known in the art. The retainer 170 may have one or more voids 172 therein to reduce the material required to form the retainer 170 or to improve durability.

The housing 101 and output assembly 150 are configured to contain a plurality of planetary gears 120 within the internal volume between the housing 101 and the output assembly 150. The planetary gears 120 have gear teeth 121 and central axial openings 122 which are configured to mate with planet gear carrier pins 151. The planetary gears 120 are held in axial alignment by the engagement of the central axial openings 122 and the planet gear carrier pins 151, but can rotate freely around the planet gear carrier pins 151. The planetary gears 120 are disposed such that no two planetary gears 120 come into contact to prevent their rotation. The gear teeth of each planetary gear 120 engage with both the gear teeth 510 of the sun gear and a gear ring formed from an inward-facing plurality of gear teeth 104 which are disposed within the interior annular wall surface 103 of the housing 101. As the sun gear rotates and engages with the planetary gears, the planetary gears travel circularly around the central axis of the shaft assembly 500 due to their engagement with the gear teeth 104 of the gear ring in the housing 101, which is fixed to the body of the rotational tool. The circular travel of the planetary gears forces the rotation of the guide pins 151 and the corresponding rotation of the components of the output assembly 150 to which the guide pins 151 are attached or integrated within. In some implementations, such as the non-limiting exemplary implementations depicted in FIGS. 5-9, the rotation of the guide pins 151 causes rotation of a planet carrier 180 and output shaft insert 168. In some implementations, such as the non-limiting exemplary implementations depicted in FIGS. 2-4 and 12-13, the rotation of the guide pins 151 causes rotation of an output shaft 152.

The relative movement between components can be improved by making one or more of the housing 101, planet gears 120, drive shaft assembly 500, or output assembly 150 out of material that has a low coefficient of friction when in contact with another surface, coating the above components with a material that has a low coefficient of friction when in contact with another surface, applying a lubricant to the above components, positioning one or more low friction spacers or washers, such as spacers 111/112, between adjacent components undergoing relative motion or rotation, or any combination of approaches in this list. One or more of the low-friction spacers may be constructed of a material or layers of material wherein after being exposed to a predetermined amount of friction and activity the material degrades or a layer is worn away exposing a layer which is easily degraded thereby adding debris to the planet gear and sun gear causing failure. In some implementations, a low friction spacer can be exposed to friction between planetary gear top 124 and housing 101, which leads to degradation of the spacer and failure of the overall system. In some implementations, a surface roughness or one or more protruding features can be provided on one or more portions of one or more surface components in order to impart a desired amount of degradation to a low friction spacer and introduce debris into the internal volume of the speed reduction assembly in order to induce failure after a predetermined amount of operation.

In some aspects, the integrated rotational speed reduction assembly 100 may be disposable. The integrated rotational speed reduction assembly 100 may be used for a predetermined number of uses. Alternatively, the integrated rotational speed reduction assembly 100 may be used for a predetermined duration of time. In some aspects, the integrated rotational speed reduction assembly 100 is intended for singular use. In further aspects, the reduction assembly is intended to be used for a predetermined number of rotations. In some aspects, the entire integrated rotational speed reduction assembly 100 is intended to be disposed of after a fixed usage period. In other aspects, portions of the integrated rotational speed reduction assembly 100 are intended to be disposed of while other portions are intended to be reused.

The drive shaft 301 may attach to a rotational tool that rotates the shaft during operation, such as a medical power tool 200. The integrated rotational speed reduction assembly 100 may accept various rotational inputs. In some aspects, it may accept inputs of up to about 2000 rpm in rotational speed. In other aspects, it may accept higher rotational speed inputs. In some aspects of the disclosure, it may accept inputs of at least about 150 rpm, in some aspects, it may accept inputs of at least about 450 rpm; in some aspects, it may accept inputs of at least about 1000 rpm; in some aspects, it may accept inputs of at least about 1250 rpm. In some aspects, it may accept inputs of up to about 1 N-m, up to about 2 N-m, up to about 3 N-m, up to about 4 N-m, up to about 5 N-m, up to about 6 N-m, up to about 7 N-m, up to about 8 N-m, up to about 9 N-m, or up to about 10 N-m.

The integrated rotational speed reduction assembly 100 can be used in methods of reducing rotational speed includes connecting a rotational tool to an integrated rotational speed reduction assembly, such as one described herein, and then operating the rotational tool. The method may further include a step of disconnecting the rotational tool from the reduction assembly. The method may further include a step of disposing of the tool, the reduction assembly, or both after an acceptable number of uses or after an acceptable duration of use. The method may further include a step of connecting the reduction assembly to a second tool. The connection of the second tool may be made before connection of the first tool, after connection of the first tool, or while the first tool is connected. In some aspects, more tools may be connected in a variety of acceptable orders. The method may further include a step of connecting a torque limiting device to the integrated rotational speed reduction assembly.

The integrated rotational speed reduction assemblies described herein can provide for predetermined rotational speed reduction ratios. The rotational speed reduction ratio is determined by the relative number of gear teeth provided on the sun gear 501, planetary gears 120, and the gear ring formed of gear teeth 104 in the housing 101, and the relative sizes of the gears. The gearing ratio can be predetermined as the ratio of (number of sun gear teeth 510 plus the number of gear ring teeth 104)/(number of sun gear teeth 510). The gearing ratio represents the reduction in rotational speed, such that, for example, a value of 5:1 indicates that an input speed of 1000 rpm would create an output speed of 200 rpm. In some implementations, the gearing ratio can be provided as about 2.5:1, about 3:1, about 3.5:1, about 4:1, about 4.5:1, about 5:1, about 5.5:1, about 6:1, about 7:1, about 8:1, about 9:1, about 10:1, or about 11:1. Input torque is increased by the gearing ratio to produce a correspondingly higher output torque (before efficiency losses).

While the method and apparatus have been described in terms of what are presently considered to be the most practical and preferred implementations, it is to be understood that the disclosure need not be limited to the disclosed implementations. It is intended to cover various modifications and similar arrangements included within the spirit and scope of the claims, the scope of which should be accorded the broadest interpretation so as to encompass all such modifications and similar structures. The present disclosure includes any and all implementations of the following claims.

It should also be understood that a variety of changes may be made without departing from the essence of the disclosure. Such changes are also implicitly included in the description. They still fall within the scope of this disclosure. It should be understood that this disclosure is intended to yield a patent covering numerous aspects of the disclosure both independently and as an overall system and in both method and apparatus modes.

Further, each of the various elements of the disclosure and claims may also be achieved in a variety of manners. This disclosure should be understood to encompass each such variation, be it a variation of an implementation of any apparatus implementation, a method or process implementation, or even merely a variation of any element of these.

Particularly, it should be understood that as the disclosure relates to elements of the disclosure, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this disclosure is entitled.

It should be understood that all actions may be expressed as a means for taking that action or as an element which causes that action.

Similarly, each physical element disclosed should be understood to encompass a disclosure of the action which that physical element facilitates.

Any patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in at least one of a standard technical dictionary recognized by artisans and the Random House Webster's Unabridged Dictionary, latest edition are hereby incorporated by reference.

In this regard it should be understood that for practical reasons and so as to avoid adding potentially hundreds of claims, the applicant has presented claims with initial dependencies only.

Support should be understood to exist to the degree required under new matter laws—including but not limited to United States Patent Law 35 USC 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular implementation, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative implementations.

Such terms should be interpreted in their most expansive forms so as to afford the applicant the broadest coverage legally permissible.

What is claimed:

1. A single use integrated rotational speed reduction assembly comprising:
    a shaft assembly comprising a drive shaft (301) and a sun gear (510) attached to said drive shaft;
    a housing;
    a plurality of planetary gears (120) each having a plurality of gear teeth; and, an output assembly (150);
    wherein one or more of said plurality of planetary gears is non-metal, and, thus, said plurality of gear teeth on each said non-metal planetary gears are also non-metal; and,
    wherein the one or more of said non-metal teeth are frangible after a predetermined number of use cycles of said non-metal teeth.

2. The single use integrated rotational speed reduction assembly of claim 1, wherein said shaft assembly provides for the mating between said housing and said output assembly via one or more retaining features provided on said shaft assembly.

3. The single use integrated rotational speed reduction assembly of claim 1, wherein at least one of said frangible, non-metal teeth will fail after a predetermined number of use cycles of said frangible, non-metal teeth.

4. The single use integrated rotational speed reduction assembly of claim 1, wherein:
    said integrated rotational speed reduction assembly is configured to receive a rotational input to said shaft assembly of up to 150 rpm, 250 rpm, 500 rpm, 750 rpm, 1000 rpm, 1250 rpm, 1500 rpm, or 2000 rpm;
    said integrated rotational speed reduction assembly is configured to receive a torque input to said shaft assembly of up to 1 N-m, up to 2 N-m, up to 3 N-m, up to 4 N-m, up to 5 N-m, up to 6 N-m, up to 7 N-m, up to 8 N-m, up to 9 N-m, or up to 10 N-m;
    said integrated rotational speed reduction assembly is configured to provide a gearing ratio such that the rotational speed is reduced between the input to said shaft assembly and the output to said output assembly by said gearing ratio and said torque input is increased between the input to said shaft assembly and the output to said output assembly by said gearing ratio; and
    said gearing ratio is provided as 2.5:1, 3:1, 3.5:1, 4:1, 4.5:1, 5:1, 5.5:1, 6:1, 7:1, 8:1, 9:1, 10:1, or 11:1.

5. The single use integrated rotational speed reduction assembly of claim 1, wherein:
    said output assembly comprises an output shaft having a plurality of pin guides, with each pin guide mating with one of said plurality of planetary gears to prevent relative axial movement between each mated pin guide and planetary gear but allowing for relative axial rotation between each mated pin guide and planetary gear;
    said housing comprises a gear ring of a plurality of gear teeth disposed on an interior surface of said housing, with said gear ring configured to engage with said gear teeth of said planetary gears; and
    said output shaft is configured to rotate in response to rotation of said shaft assembly, via engagement between said sun gear and said planetary gears, engagement between said planetary gears and said gear ring.

6. The integrated rotational speed reduction assembly of claim 1, wherein:
    said output assembly comprises a planetary gear carrier having a plurality of pin guides and a retainer;
    each pin guide mates with one of said plurality of planetary gears to prevent relative axial movement between each mated pin guide and planetary gear but allows for relative axial rotation between each mated pin guide and planetary gear;
    said housing comprises a gear ring of a plurality of gear teeth disposed on an interior surface of said housing, with said gear ring configured to engage with said gear teeth of said planetary gears;
    said planetary gear carrier mates with one of the retaining features of said shaft assembly;
    said retainer mates with said housing and surrounds at least a portion of said planetary gear carrier; and
    said planetary gear carrier is configured to rotate in response to rotation of said shaft assembly, via engagement between said sun gear and said planetary gears, and engagement between said planetary gears and said gear ring.

7. A single use speed reduction system comprising:
    a shaft assembly comprising:
        a drive shaft (301);
        a shaft having a sun gear thereon;
        a housing having an interior annular wall surface (103) with a gear ring (104) thereon; a plurality of planetary gears (120) each having a plurality of gear teeth;
        an output assembly (150);
        wherein the shaft is mated with the housing; wherein one or more of gears is non-metal;
        wherein one or more non-metal teeth are frangible after a predetermined number of use cycles of said non-metal teeth;
    wherein said one or more non-metal gears comprise one or more gamma-radiation-sensitive materials in at least a region; and
    wherein said one or more gamma-radiation-sensitive materials undergo embrittlement at an exposure of less than one of 200 kGy, 150 kGy, 100 kGy, 95 kGy, 90 kGy, 85 kGy, 80 kGy, 75 kGy, 70 kGy, 65 kGy, 60 kGy, 55 kGy, 50 kGy, 45 kGy, 40 kGy, 35 kGy, 30 kGy, 25 kGy, 20 kGy, 15 kGy 10 kGy, and 5 kGy.

8. The single use speed reduction system or claim 7 wherein said plurality of planetary gears are disposed such that no two planetary gears come into contact to prevent their rotation and said gear teeth of each planetary gear engages with both said gear teeth of said sun gear and a gear ring.

9. The single use speed reduction system of claim 8 wherein at least one of said frangible, non-metal teeth will fail after a predetermined number of use cycles of said frangible, non-metal teeth.

10. The single use speed reduction system of claim 8, further comprising one or more spacers disposed between one or more pairs of components configured for relative motion, wherein the one or more spacers are configured to degrade and produce debris after a predetermined number of use cycles.

11. The single use speed reduction system of claim 7, wherein:
  said single use speed reduction system is configured to receive a rotational input to said shaft assembly of up to 150 rpm, 250 rpm, 500 rpm, 750 rpm, 1000 rpm, 1250 rpm, 1500 rpm, or 2000 rpm;
  said single use speed reduction system is configured to receive a torque input to said shaft assembly of up to 1 N-m, up to 2 N-m, up to 3 N-m, up to 4 N-m, up to 5 N-m, up to 6 N-m, up to 7 N-m, up to 8 N-m, up to 9 N-m, or up to 10N-m;
  said single use speed reduction system is configured to provide a gearing ratio such that the rotational speed is reduced between the input to said shaft assembly and the output to said output assembly by the gearing ratio and the torque input is increased between said input to said shaft assembly and said output to said output assembly by said gearing ratio; and
  said gearing ratio is provided as 2.5:1, 3:1, 3.5:1, 4:1, 4.5:1, 5:1, 5.5:1, 6:1, 7:1, 8:1, 9:1, 10:1, or 11:1.

12. The single use speed reduction system of claim 7, wherein said one or more gamma-radiation-sensitive materials comprises polytetrafluoroethylene (PTFE), fluorinated ethylene propylene (FEP) polyoxymethylene/polyacetals, aliphatic and amorphous grades of nylon polyamides, polymethylpentene, polypropylenes, or combinations thereof.

13. The single use speed reduction system of claim 7, wherein said one or more gamma-radiation-sensitive materials are incorporated throughout the one or more non-metal gears as a wt/wt % of the gamma-radiation-sensitive material in all regions of the one or more non-metal gears.

14. The single use speed reduction system of claim 7, wherein said one or more gamma-radiation-sensitive materials can be incorporated in said one or more non-metal gears in a particular region of said one or more non-metal gears while the remaining regions of said one or more non-metal gears are substantially free of any gamma-radiation-sensitive material, providing a desired wt/wt % for said one or more non-metal gears when considered as a whole.

15. The single use speed reduction system of claim 13, wherein said wt/wt % of said one or more gamma-radiation-sensitive materials in said one or more non-metal gears is 5%, 10%, 15%, 20%, 25%, 30%, 35%, 40%, 45%, 50%, 55%, 60%, 65%, 70%, 75%, 80%, 85%, 90%, 95%, or 100%.

* * * * *